(12) United States Patent
Harrold

(10) Patent No.: US 6,413,246 B1
(45) Date of Patent: Jul. 2, 2002

(54) METERED, MECHANICALLY PROPELLED, LIQUID DISPENSER

(76) Inventor: John E. Harrold, 27 Milford Rd., Bloomsbury, NJ (US) 08804

( * ) Notice: Subject to any disclaimer, the term of this patent is extended or adjusted under 35 U.S.C. 154(b) by 0 days.

(21) Appl. No.: 09/574,191

(22) Filed: May 18, 2000

(51) Int. Cl.$^7$ .............................................. A61M 35/00
(52) U.S. Cl. ...................................... 604/298; 604/135
(58) Field of Search .......................... 604/131, 134–136, 604/298, 294, 245–249, 207–211

(56) References Cited

U.S. PATENT DOCUMENTS

| | | | | |
|---|---|---|---|---|
| 3,754,687 A | * | 8/1973 | Norton | 222/309 |
| 3,934,585 A | * | 1/1976 | Maurice | 128/225 |
| 4,091,677 A | * | 5/1978 | Oshikubo | 73/425.6 |
| 5,226,895 A | * | 7/1993 | Harris | 604/208 |
| 5,267,986 A | | 12/1993 | Py | 604/294 |
| 5,401,259 A | | 3/1995 | Py | 604/294 |
| 5,613,957 A | | 3/1997 | Py | 604/294 |
| 5,685,869 A | | 11/1997 | Py | 604/294 |

\* cited by examiner

Primary Examiner—Anhtuan T. Nguyen
Assistant Examiner—Ann Y Lam
(74) Attorney, Agent, or Firm—Kenneth P. Glynn, Esq.

(57) ABSTRACT

The present invention relates to a metered, mechanically propelled, liquid dispenser. It has a main body cylinder having liquid and liquid advancing mechanism for advancing the liquid into a metered dosage dispensing chamber. There is a cocking mechanism which includes a lock pin, a stressed slot and a rest slot. When the cocking mechanism is locked, the advancing means is moved and liquid is ready for firing from the metered dosage dispensing chamber through a dispensing orifice. The cocking mechanism is slowly rotated while holding the main body cylinder vertically and the pin is manually moved into the rest slot thereby causing a plunger to be forced by a spring to push against a stop on a trigger which advances the trigger to rapidly force the liquid out of the metered dosage dispensing chamber through the dispensing orifice. The dispensing orifice includes a one-way valve which allows the liquid to be dispensed while preventing air from returning to the device.

20 Claims, 2 Drawing Sheets

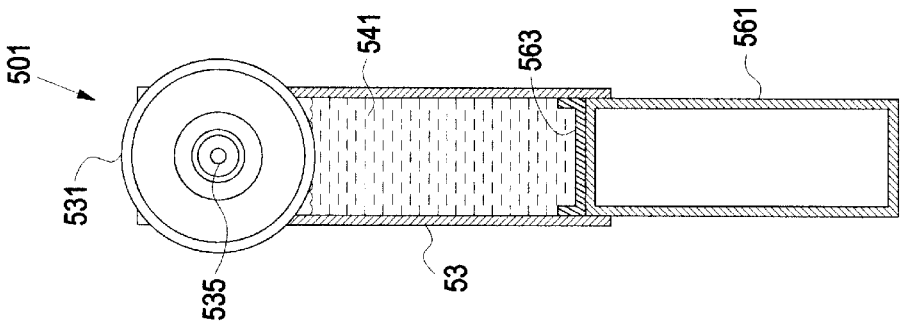
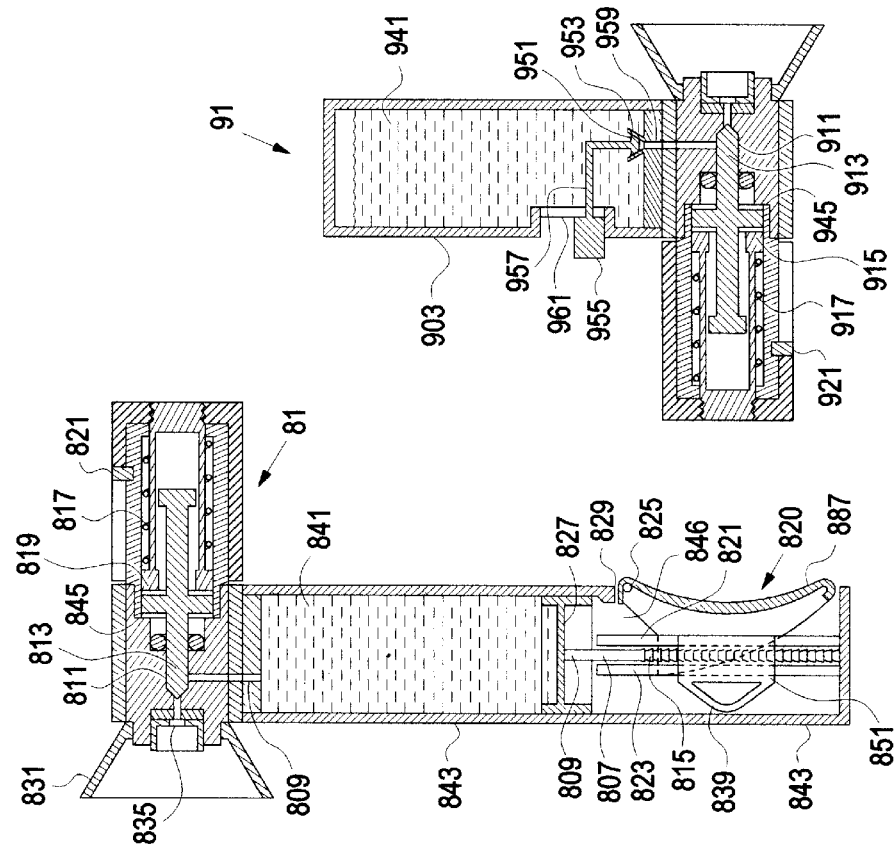
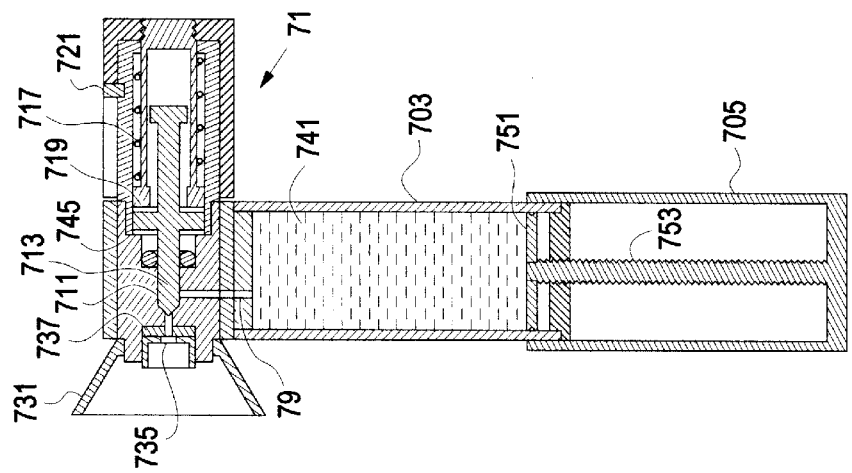

METERED, MECHANICALLY PROPELLED, LIQUID DISPENSER

BACKGROUND OF THE INVENTION

1. Field of the Invention

The present invention relates to metered, mechanically propelled, liquid dispensers, and, more particularly, to those dispensers which have a plunger activated by a cocking mechanism and having a trigger mechanism for dispensing a liquid stream or fine mist activated by the plunger. In particular, the present invention includes a metered amount of the liquid to be dispensed.

2. Information Disclosure Statement

The following patents are representative of metered, mechanically propelled, liquid dispensers:

U.S. Pat. No. 3,934,585 to David M. Maurice discloses a method and apparatus for applying therapeutic eye drops to the eye by metering a predetermined volume of fluid and rapidly applying a pressure to one end of the metered fluid for forcing the fluid from a nozzle of means defining a small passageway such as and open-ended tube as a droplet having sufficient velocity to travel a generally horizontal distance in space to the eye. Unit dose application and multiple dose applications are included and provision is made for preventing anticipatory blinking of the eye during self-administration.

U.S. Pat. No. 5,267,986 describes and illustrates a cartridge for actuating a piston-like or accordion-like dispenser-vial for applying medication to any eye. The cartridge includes a housing for holding the dispenser-vial and a telescoping cylinder for compressing the dispenser-vial in the longitudinal direction to actuate the vial. The cartridge includes a locking mechanism for locking the telescoping cylinder to restrict its movement and a trigger mechanism for releasing the cylinder from the locked position so that a drop is released form the dispenser. The housing includes a finger for engaging the lower eyelid and exposing the conjunctival cul de sac.

U.S. Pat. No. 5,401,259 discloses a cartridge for actuating a piston-like or accordion-like dispenser-vial for a applying medicament to an eye. The cartridge includes a housing for holding the dispenser-vial and a telescoping cylinder for compressing the dispenser-vial in the longitudinal direction to activate the vial. The cartridge includes a locking mechanism for locking the telescoping cylinder to restrict its movement and a lever mechanism for releasing the cylinder from the locked position so that a drop is released from the dispenser. The housing includes a finger for engaging the lower eyelid and exposing the conjunctival cul-de-sac.

U.S. Pat. No. 5,613,957 to Daniel Py discloses an apparatus used for applying medicament to an eye and to store the medicament in a medicament chamber. A nozzle is coupled in fluid communication with the medicament chamber and is formed by an outer nozzle portion and an inner nozzle portion received within the outer nozzle portion. A tight interface is defined between the inner nozzle portion and the outer nozzle portion and is normally in a closed position to prevent the passage of medicament through the nozzle. The interface opens in response to the flow of medicament of sufficient pressure into it to permit the passage of medicament through the nozzle for release into the eye.

U.S. Pat. No. 5,685,869 to Daniel Py describes and illustrates an apparatus used to apply medicament to an eye and to store the medicament in a medicament chamber. A nozzle is couples in fluid communication with the medicament chamber and is formed by an outer nozzle portion and an inner nozzle portion received within the outer nozzle portion. A seam is formed by the interface of the inner nozzle portion and the outer nozzle portion and is normally in a closed position to prevent the passage of medicament through the nozzle. The seam opens in response to the flow of medicament or sufficient pressure into the seam to permit the passage of medicament through the nozzle for release into the eye.

Notwithstanding the prior art, the present invention is neither taught nor rendered obvious thereby.

SUMMARY OF THE INVENTION

The present invention relates to a metered, mechanically propelled, liquid dispenser. It has a main body cylinder having liquid and liquid advancing means for advancing the liquid into a metered dosage dispensing chamber. The metered dosage dispensing chamber receives a metered amount of the liquid. It includes a metered dosage dispensing chamber stop and is connected to the main body cylinder and a dispensing orifice on a forward top end of the liquid dispenser. An amount of the liquid is received from the main body cylinder and is advanced into the metered dosage dispensing chamber by advancing the advancing means.

There is a cocking mechanism located in a top rear end of the liquid dispenser and includes a lock means, a stressed position means and a resting position means such that the cocking mechanism is in a locked position when the lock means is located within the stressed position means, and a spring located between a plunger means and the cocking mechanism is kept in a stressed position.

In addition, there is a dispensing means located between the metered dosage dispensing chamber and the cocking mechanism. It includes the plunger means which is attached to the cocking mechanism, the spring means, and a trigger means located partially within the metered dosage dispensing chamber. There is also a stop means located on the trigger means. The dispensing means allows the liquid to be forced out of the metered dosage dispensing chamber through the dispensing orifice. The dispensed liquid may be in the form of a fine spray or a liquid stream.

When the cocking mechanism is locked, in order to fill the metered dosage dispensing chamber and to trigger the trigger means, the liquid advancing means is advanced to advance the liquid into the metered dosage dispensing chamber. Next, the cocking mechanism is slowly rotated while holding the main body cylinder vertically and the lock means is manually moved away from the stressed position means and into the rest position means thereby causing the plunger means to be forced by the spring means and to push the stop means and to advance the trigger means to a metered dosage dispensing chamber stop and to rapidly force the liquid out of the metered dosage dispensing chamber through said dispensing orifice.

The liquid advancing means may be a rotatable means, push-up means, gravity-feed means, or ratchet means. In some preferred embodiments, there are indications for advancing a metered amount of the liquid into the metered dosage dispensing chamber. One embodiment includes indica on a base rotatable handle while another includes one ratchet length movement as the metered dosage.

BRIEF DESCRIPTION OF THE DRAWINGS

The present invention should be more fully understood when the specification herein is taken in conjunction with the drawings appended hereto wherein:

FIG. 6 shows a front view of another embodiment of a present invention metered, mechanically propelled, liquid dispenser having another rotatable liquid advancing means;

FIG. 7 shows a side partially cut view of another embodiment of a present invention metered, mechanically propelled, liquid dispenser having a ratchet liquid advancing means;

FIG. 8 shows a side partially cut view of still yet another embodiment of a present invention metered, mechanically propelled, liquid dispenser having a gravity-feed liquid advancing means; and FIG. 9 shows a front view of still yet another embodiment of a present invention metered, mechanically propelled, liquid dispenser having a push up advancing means.

DETAILED DESCRIPTION OF THE PRESENT INVENTION

Figure 1:
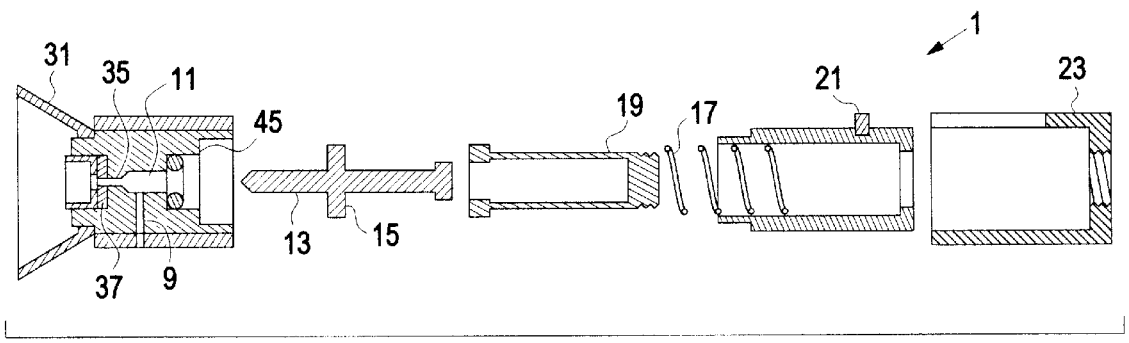
FIG. 1 shows a side cut view of a top portion of a preferred embodiment of a present invention metered, mechanically propelled, liquid dispenser blown apart
Figure 2:
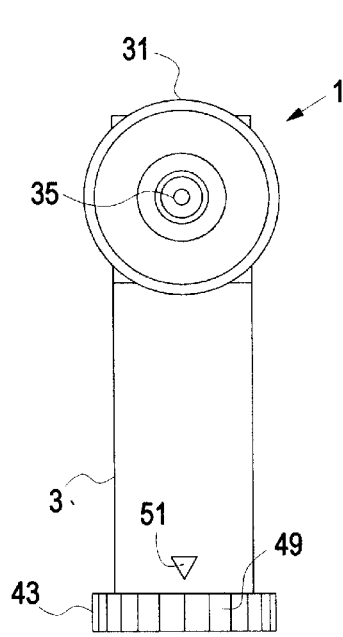
FIG. 2 shows a front view thereof.

The present invention relates to metered, mechanically propelled, liquid dispensers. It has a plunger activated by a cocking mechanism, which triggers a trigger for firing liquid through a dispensing orifice. The liquid may be dispensed in the form of a liquid stream or a fine mist.

There is a liquid advancing means which advances the liquid in a main body cylinder into a metered dosage dispensing chamber the liquid from the metered dosage dispensing chamber is dispensed through the dispensing orifice, once the cocking mechanism is unlocked and the trigger is fired.

The dispensing orifice includes a one-way valve which allows the liquid in the form of a stream or fine mist to flow out of the dispensing orifice but prevent air from returning to the chamber. In this way, preservative-free liquids may be used.

The present invention is intended primarily for the dispensing of liquid streams and fine mists to the eye. However, it could also be used for the dispensing of liquids and fine sprays to other body parts, as well as for the dispensing of antiseptics and the like to open wounds.

Referring now to FIGS. 1, 2, 3, and 4, there is shown a side cut view of a top portion blown apart, a front view, a side partially cut view in a release and dispense form, and a side partially cut view of a top portion in an open and lock form, respectively, of a preferred embodiment of a present invention metered. mechanically propelled, liquid dispenser 1. The device 1 includes a main body cylinder 3 having liquid 41 to be dispensed, a metered dosage dispensing chamber 11 for receiving a metered amount of the liquid 41, a cocking mechanism 23 located in a top rear end of the liquid dispenser 1 and a dispensing means for dispensing the liquid 41 in the metered dosage dispensing chamber 11 through a dispensing orifice. The dispensing orifice includes a nozzle 35, a projection member 31 surrounding the nozzle 35 and a one-way valve 37. The one-way valve 37 allows the liquid 41 to dispense through the nozzle 35 but prevents air from returning into the device 1. The liquid 41 may be preservative free.

The main body cylinder 3 also includes a liquid advancing means. In this case, the liquid advancing means is a rotation means having a bottom rotatable base 43 which includes a screw rod 47 extending upwardly within the main body cylinder 3 and being attached to an elevator cup 7 for rotation to advance the liquid 41 into the metered dosage dispensing chamber. Bottom rotatable base 43 has a plurality of indicia lines 49 for measuring the rotation for a metered amount of the liquid 41. The distance between two indicia lines 49 marks a metered amount of liquid which moves into the metered dispensing chamber when the bottom rotatable base 43 is rotated one indicia line distance. Triangular indicator 51 shows a metered rotation by indicating when the next indicia has been reached.

Other liquid advancing means include a push up liquid advancing means, ratchet liquid advancing means, gravity-feed liquid advancing means and the like, which will be described hereinafter. The metered dosage dispensing chamber 11 includes a stop 45 for stopping a trigger means.

A connecting means 9, in this case a tube, connects the main body cylinder 3 with the metered dosage dispensing chamber 11. The connecting means 9 allows the liquid 41 to flow from the main body cylinder 3 and flow into the metered dosage dispensing chamber 11 when the metered dosage dispensing chamber 11 is open and a cocking mechanism is in a locked position, which is further defined hereinafter.

The cocking mechanism 23 includes a lock means, a stressed position means and a resting position means. In this case, the lock means is a pin 21, the stressed position means is a slot with one side open 25 and the resting position means is U-shaped slot 33. Other lock means and stressed and resting position means include hook and loops, sliders with interlocking pieces, and the like.

The dispensing means includes a plunger 19, a spring means 17, a trigger 13 and a stop 15 which is located on the trigger 13. The plunger 19 is attached to the cocking mechanism 23. The spring means 17 is located between the plunger 19 and the cocking mechanism 23. The trigger 13 is adapted to partially fit into the metered dosage dispensing chamber 11.

Figure 3:
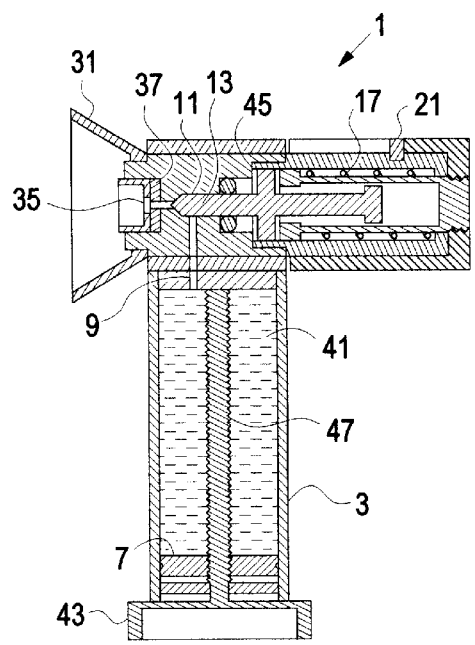
FIG. 3 shows a side partially cut view of the present invention metered, mechanically propelled, liquid dispenser shown in FIG. 1 with a trigger means being triggered and a liquid being released.
Figure 4:
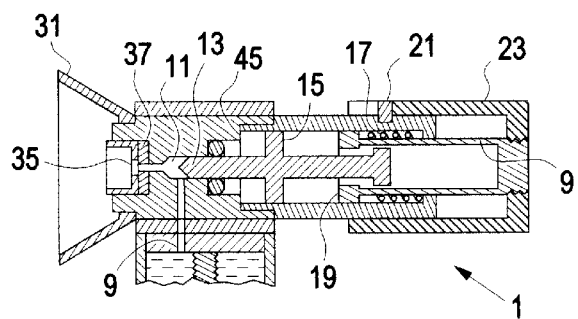
FIG. 4 shows a side partially cut view of a top portion of the present invention metered, mechanically propelled, liquid dispenser shown in FIG. 1 with a metered dosage dispensing chamber open and a cocking mechanism locked.

Referring now to FIGS. 3 and 4, there is shown the operation of the device 1. FIG. 3, shows the device 1 with the liquid being dispensed through the dispensing orifice 35 while FIG. 4 shows a top portion of the device 1 with the metered dosage dispensing chamber 11 filled and ready to fire. As shown, the trigger 13 advances with the stop means 15, when the trigger 13 is fired. In addition, the trigger 13 and the stop means 15 are shown as integral parts.

Figure 5:
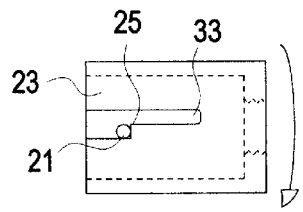
FIG. 5 shows a partial view of the cocking mechanism shown in FIGS. 1–4.

In operation, when liquid 41 is advanced by rotating liquid advancing means 43 by one indicia, metered dosage dispensing chamber 11 is filled with a small amount of metered liquid 41. In order to dispense the liquid 41, trigger 13 is fired by slowly rotating the cocking mechanism 23 so that the lock means 21 is moved from the stressed position means 25 to the rest position means 33, thereby firing the trigger 13. FIG. 5 shows the operation of the cocking mechanism 23. In rotating the lock means 21 to the rest position means 33, the plunger 19 is forced by the spring means 17 to push against the stop means 15 on the trigger 13 so that the trigger 13 advances into the metered dosage dispensing chamber 11 and is stopped by metered dosage dispensing chamber stop 45, as shown in FIG. 3. Because the firing distance from the plunger 19 to the stop 15 is relatively large in comparison to the firing distance from the trigger 13 to the metered dosage dispensing chamber stop 45, the liquid 41 moves rapidly from the dispensing dosage dispensing chamber 11 through the dispensing nozzle. The dispensed liquid may be in the form of a fine mist or a liquid stream. Once the liquid 41 is dispensed, the cocking mechanism 23 is locked by rotating lock pin 21 to stressed position means 25 so that the metered dosage dispensing chamber 11 can be filled, as shown in FIG. 4.

Referring now to FIG. 6, there is shown a side partially cut view of another embodiment of a present invention metered mechanically propelled, liquid dispenser 71 having another rotatable liquid advancing means 705. In this embodiment, similar parts to the embodiment shown in FIG. 1 are identically numbered, but beginning with "7".

Rotatable liquid advancing means, in this case, rotatable cylinder 705 is rotated to advance a screw rod 753 upward through main body cylinder 703 and therefore, advance elevator cup 751 and advance liquid 741 into the metered dosage dispensing chamber 711. The dispensing of liquid 741 through the dispensing orifice is the same as that described in FIGS. 1–5.

In FIG. 7, there is shown a side partially cut view of another embodiment of a present invention metered. mechanically propelled, liquid dispenser 81 having a ratchet liquid advancing means. In this embodiment, similar parts to the embodiment shown in FIG. 3 are identically numbered, but beginning with "8".

The ratchet liquid advancing means includes a vertical support column 807 having a vertical ratchet track 809 with ratchets such as ratchet 215 and is connected to push plate 827. There are guide columns 821 and 823 inside housing 843 in which the vertical support column 807 may move upwardly and downwardly, except for its restraint and advance by ratchet trigger component 820, discussed below.

The ratchet trigger component 820 acts as a trigger, as a ratchet member and as a spring. It includes a trigger lever 887 which is movably connected to housing 843, i.e. cut out 829 of lever 887 is snapped on or otherwise connected to housing 843 at peg 825 so as to be rotatable or swingable into housing 843. Ratchet advancer fin 845 interacts with ratchet track 809 such that when lever 887 is pushed in, advancer fin 846 swings up and advances and holds track 809 up one ratchet length, thereby advancing push plate 827 and the liquid 841.

Not only is the trigger component 820 functioning as a trigger and a ratcheting advancer, but it also includes a spring plate 851 with a springy, flexible portion 839. This automatically pushes lever 887 back to its first position by springing back from wall 843 so that it and the ratchet advancer fin 846 are reset for the next advance.

Once the liquid advancing means is advanced, or, in this case, the ratchet is advanced, the operation of the dispensing means is the same as that described by FIGS. 1–5. In a preferred embodiment, advancing the ratchet means by one ratchet length will cause a metered amount of the liquid 841 to enter the metered dosage dispensing chamber 811.

In FIG. 8, there is shown a side partially cut view of still yet another embodiment of a present invention metered, mechanically propelled, liquid dispenser 91 having a gravity-feed liquid advancing means. In this embodiment, similar parts to the embodiment shown in FIG. 3 are identically numbered, but beginning with "9".

The gravity-feed liquid advancing means includes a slider 955, an L-shaped bar 957 attached to the slider 955 and a liquid-tight plug 953 attached to one end of the L-shaped bar 957. The liquid-tight plug 953 is sized and shaped to fit within a funnel 953, which is attached to a connecting tube 959. The connecting tube 959 connects a main body cylinder chamber 903 with a metered dosage dispensing chamber 911. To allow the liquid 941 into the metered dosage dispensing chamber 911, the slider 955 is moved upward within the sliding cut-out 961, which causes the liquid-tight plug 953 to be removed from the funnel 959 and to allow liquid 941 to flow into the metered dosage dispensing chamber 911. To prevent the liquid 941 from flowing into the metered dosage dispensing chamber 903, the slider 955 is moved downward causing the liquid-tight plug 953 to be placed within the funnel 959. Once the liquid advancing means is advanced, or, in this case, the gravity-feed is opened, the operation of the dispensing means is the same as that described by FIGS. 1–6.

FIG. 9 shows a front, partially cut view of still yet another embodiment of a present invention metered. mechanically propelled, liquid dispenser 501 having a push-up liquid advancing means. In this embodiment, similar parts to the embodiment shown in FIG. 1 are identically numbered, but beginning with "5".

The push-up liquid advancing means includes a pusher 561 which fits within a main body cylinder 53 and is sized and shaped to push the bottom 563 of the main body cylinder 53 upward and advance liquid 541 in the main body cylinder 53 into the metered dosage dispensing chamber.

In a preferred embodiment, indicia lines on the pusher 561 indicate a metered amount of the liquid being advanced into the metered dosage dispensing chamber. Once the liquid advancing means is advanced, or, in this case, the push-up feed is pushed, the operation of the dispensing means is the same as that described by FIGS. 1–6.

Obviously numerous possibilities and variations of the above invention are possible in light of the above teachings. For example, different ratchet mechanisms may be used other than the one described herein. It is therefore understood that within the scope of the appended claims, the invention may be practiced otherwise than as specifically practiced herein.

What is claimed is:

1. A metered, mechanically propelled, liquid dispenser which comprises:
   (a) a main body cylinder having liquid and liquid advancing means for advancing the liquid into a metered dosage dispensing chamber;
   (b) a metered dosage dispensing chamber for receiving a metered amount of the liquid and including a dispensing nozzle for dispensing the liquid out of said liquid dispenser;
   (c) a connecting means for connecting said main body cylinder to said metered dosage dispensing chamber, wherein said connecting means is located on a forward end of said liquid dispenser and permitting an amount of the liquid received from said main body cylinder to be advanced into said metered dosage dispensing chamber by advancing said advancing means;
   (d) a metered dosage dispensing chamber stop located within said metered dosage dispensing chamber, and being adapted to stop a trigger means when moved;
   (e) trigger means located partially within said metered dosage dispensing chamber and having a trigger stop wherein said trigger stop stops a plunger means from moving after a spring means is caused to move to an unstressed position and move said plunger means toward said trigger stop, and wherein said trigger stop is separate from said metered dosage dispensing chamber stop;

(f) a cocking mechanism located in a rear end of said liquid dispenser and having a lock means, a stressed position means and a resting position means wherein said cocking mechanism is initially kept in a locked position when said lock means is located at said stressed position means;

(g) plunger means attached to said cocking mechanism and being sized and shaped to hit against said trigger stop when said plunger means is caused to be move forwardly within said liquid dispenser;

(h) spring means cooperating with said plunger means and said cocking mechanism;

wherein when said cocking mechanism is locked, in order to fill said metered dosage dispensing chamber and to trigger said trigger means, said liquid advancing means is advanced to advance the liquid into said metered dosage dispensing chamber and then said cocking mechanism is slowly rotated while holding said main body cylinder vertically and said lock means is moved away from said stressed position means and into said rest position means thereby causing said plunger means to be forced by said spring means and to push said trigger stop and to advance said trigger means to said metered dispensing chamber stop, thereby forcing the liquid rapidly out of said metered dosage dispensing chamber through said dispensing nozzle, and wherein a first firing distance of said plunger means to said trigger stop and a second firing distance of said trigger means to said dispensing chamber stop are such that said second firing distance may be relatively short in comparison to said first firing distance whereby the liquid moves rapidly from said metered dosage dispensing chamber and out of said dispensing nozzle.

2. The metered, mechanically propelled, liquid dispenser of claim 1 wherein said liquid advancing means is selected from the group consisting of rotatable means, push-up means, gravity-feed means, and ratchet means.

3. The metered, mechanically propelled, liquid dispenser of claim 1 wherein said liquid advancing means includes a bottom rotatable base and a screw rod and an elevator cup for rotation to advance the liquid into said metered dosage dispensing chamber.

4. The metered, mechanically propelled, liquid dispenser of claim 2 wherein said trigger means and said trigger stop move concurrently with each other.

5. The metered, mechanically propelled, liquid dispenser of claim 4 wherein said cocking mechanism is selected from the group consisting of pins and slots, hooks and loops, and sliders.

6. The metered, mechanically propelled, liquid dispenser of claim 5 wherein said trigger stop includes at least two protrusions extending beyond said trigger means.

7. The metered, mechanically propelled, liquid dispenser of claim 6 wherein a one-way valve is in cooperation with said dispensing nozzle whereby said one-way valve allows the liquid to dispense through said dispensing nozzle and prevents air from returning into the device.

8. The metered, mechanically propelled, liquid dispenser of claim 2 wherein said rotatable means includes a rotatable base wherein said rotatable base includes indicia for marking a metered amount of the liquid entering said metered dosage dispensing chamber.

9. The metered, mechanically propelled, liquid dispenser of claim 7 wherein said resting position means is a U-shaped slot.

10. The metered, mechanically propelled, liquid dispenser of claim 9 wherein said stressed position means is a slot with one side open.

11. A metered, mechanically propelled, liquid dispenser which comprises:

(a) a main body cylinder having liquid and liquid advancing means for advancing the liquid into a metered dosage dispensing chamber;

(b) a metered dosage dispensing chamber for receiving a metered amount of the liquid and including a dispensing nozzle for dispensing the liquid out of said liquid dispenser;

(c) a connecting means for connecting said main body cylinder to said metered dosage dispensing chamber, wherein said connecting means is located on a forward end of said liquid dispenser and permitting an amount of the liquid received from said main body cylinder to be advanced into said metered dosage dispensing chamber by advancing said advancing means;

(d) a metered dosage dispensing chamber stop located within said metered dosage dispensing chamber and being adapted to stop a trigger means when moved;

(e) trigger means located partially within said metered dosage dispensing chamber and having a trigger stop wherein said trigger stop stops a plunger means from moving after a spring means is caused to move to an unstressed position and move said plunger means toward said trigger stop, and wherein said trigger stop is separate from said metered dosage dispensing chamber stop;

(f) a cocking mechanism located in a rear end of said liquid dispenser and having a lock means, a stressed position means and a resting position means wherein said cocking mechanism is initially kept in a locked position when said lock means is located at said stressed position means;

(g) plunger means attached to said cocking mechanism and being sized and shaped to hit against said trigger stop when said plunger means is caused to be moved into a forward portion of said liquid dispenser;

(h) spring means cooperating with said plunger means and said cocking mechanism;

wherein said trigger means and said trigger stop means are integral parts whereby said trigger means and said trigger stop means move concurrently;

wherein when said cocking mechanism is locked, in order to fill said metered dosage dispensing chamber and to trigger said trigger means, said liquid advancing means is advanced to advance the liquid into said metered dosage dispensing chamber and then said cocking mechanism is slowly rotated while holding said main body cylinder vertically and said lock means is moved away from said stressed position means and into said rest position means thereby causing said plunger means to be forced by said spring means and to push said trigger stop and to advance said trigger means to said metered dispensing chamber stop, to force the liquid rapidly out of said metered dosage dispensing chamber through said dispensing nozzle, and wherein a first firing distance of said plunger means to said trigger stop and a second firing distance of said trigger means to said dispensing chamber stop are such that said second firing distance may be relatively short in comparison to said first firing distance whereby the liquid moves rapidly from said metered dosage dispensing chamber and out of said dispensing nozzle.

12. The metered, mechanically propelled, liquid dispenser of claim 11 wherein said liquid advancing means is selected from the group consisting of rotatable means, push-up means, gravity-feed means, and ratchet means.

13. The metered, mechanically propelled, liquid dispenser of claim 11 wherein said liquid advancing means includes a bottom rotatable base and a screw rod and an elevator cup for rotation to advance the liquid into said metered dosage dispensing chamber.

14. The metered, mechanically propelled, liquid dispenser of claim 12 wherein a one-way valve is in cooperation with said dispensing nozzle whereby said one-way valve allows the liquid to dispense through said dispensing nozzle and prevents air from returning into the device.

15. The metered, mechanically propelled, liquid dispenser of claim 14 wherein said cocking mechanism is selected from the group consisting of pins and slots, hooks and loops, and sliders.

16. The metered, mechanically propelled, liquid dispenser of claim 15 wherein said trigger stop includes at least two protrusions extending beyond said trigger means.

17. The metered, mechanically propelled, liquid dispenser of claim 12 wherein said rotatable means includes a rotatable base wherein said rotatable base includes indicia for marking a metered amount of the liquid entering said metered dosage dispensing chamber.

18. The metered, mechanically propelled, liquid dispenser of claim 16 wherein said resting position means is a U-shaped slot.

19. The metered, mechanically propelled, liquid dispenser of claim 18 wherein said stressed position means is a slot with one side open.

20. The metered, mechanically propelled, liquid dispenser of claim 19 wherein a projection member surrounds said dispensing nozzle.

* * * * *